US00PP31372P2

(12) United States Plant Patent
Hansen

(10) Patent No.: US PP31,372 P2
(45) Date of Patent: Jan. 14, 2020

(54) ***DELOSPERMA* PLANT NAMED 'PUMPKIN PERFECTION'**

(50) Latin Name: ***Delosperma* hybrid**
Varietal Denomination: Pumpkin Perfection

(71) Applicant: Christopher M. Hansen, Zeeland, MI (US)

(72) Inventor: Christopher M. Hansen, Zeeland, MI (US)

( * ) Notice: Subject to any disclaimer, the term of this patent is extended or adjusted under 35 U.S.C. 154(b) by 0 days.

(21) Appl. No.: 16/350,509

(22) Filed: Nov. 26, 2018

(51) Int. Cl.
*A01H 5/02* (2018.01)
*A01H 6/00* (2018.01)

(52) U.S. Cl.
USPC ..... Plt./422
CPC ..... *A01H 6/00* (2018.05)

(58) Field of Classification Search
USPC ..... Plt./422
See application file for complete search history.

*Primary Examiner* — Anne Marie Grunberg
(74) *Attorney, Agent, or Firm* — Penny J. Aguirre

(57) ABSTRACT

A new cultivar of *Delosperma* plant named 'Pumpkin Perfection' that is characterized by its floriferous blooming habit, its orange flowers with white centers, its very compact and tight mounds of foliage that do not become long or leggy during the summer growing months, its strong re-blooming habit during the entire growing season and into late fall, its small plant size, its uniform rooting habit, and its uniform blooming period with other plants in the series.

2 Drawing Sheets

Botanical classification: *Delosperma* hybrid.
Variety denomination: 'Pumpkin Perfection'.

CROSS REFERENCE TO RELATED APPLICATIONS

This application is co-pending with U.S. Plant Patent Applications filed for plants derived from the same breeding program that are entitled *Delosperma* Plant Named 'Banana Blast' (U.S. Plant patent application Ser. No. 16/350,513), *Delosperma* Plant Named 'Coconut Crush' (U.S. Plant patent application Ser. No. 16/350,512), *Delosperma* Plant Named 'Fig Fusion' (U.S. Plant patent application Ser. No. 16/350/511), *Delosperma* Plant Named 'Saucy Strawberry' (U.S. Plant patent application Ser. No. 16/350,514), and *Delosperma* Plant Named 'Tangerine Tango' (U.S. Plant patent application Ser. No. 16/350,510).

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102.(b)(1).

BACKGROUND OF THE INVENTION

The present invention relates to a new and distinct cultivar of *Delosperma* plant of hybrid origin, botanically known as *Delosperma* 'Pumpkin Perfection' and will be referred to hereinafter by its cultivar name, 'Pumpkin Perfection'. The new cultivar of *Delosperma* is a hardy herbaceous perennial grown for use as a landscape and container plant and is particularly suitable as a groundcover.

'Pumpkin Perfection' arose from an ongoing breeding program by the Inventor in Hudsonville, Mich. The objective was to obtain a new series of *Delosperma* cultivars with more floriferous blooming habits, smaller and more compact and uniform plant habits, and blooming periods that are the same amongst all cultivars in the series when grown under the same conditions.

The Inventor made a controlled cross in July of 2014 in his test garden in Hudsonville, Mich. between an unnamed proprietary plant from the Inventor's breeding program, reference no. 288-6, as the female parent and pollen that was pooled from unnamed proprietary plants of *Delosperma* as the male parent. The exact male parent is therefore unknown. The Inventor selected 'Pumpkin Perfection' as a single unique plant in June of 2016 from the resulting seedlings.

Asexual reproduction of the new cultivar was first accomplished by stem tip cuttings in April of 2015 in Hudsonville, Mich. Asexual propagation by stem tip cuttings has determined that the characteristics are stable and reproduced true to type in successive generations.

SUMMARY OF THE INVENTION

The following traits have been repeatedly observed and are determined to be the characteristics of the new cultivar. These attributes in combination distinguish 'Pumpkin Perfection' as a unique cultivar of *Delosperma*.

1. 'Pumpkin Perfection' exhibits a floriferous blooming habit with an average of 47 flowers per plant as a 10-week-old plant grown in a 1-quart container started from a 128-cell plug.
2. 'Pumpkin Perfection' exhibits orange flowers with white centers.
3. 'Pumpkin Perfection' exhibits very compact and tight mounds of foliage that do not become long or leggy during the summer growing months.

4. 'Pumpkin Perfection' exhibits strong re-bloom during the entire growing season and into late fall.
5. 'Pumpkin Perfection' exhibits a small plant size reaching an average of 3.8 cm in height and 38 cm in width.
6. 'Pumpkin Perfection' exhibits uniform rooting that occurs in just 10 days.
7. 'Pumpkin Perfection' exhibits a uniform blooming period with other plants in the series.

The seed parent plant of 'Pumpkin Perfection', no. 288-6, differs from 'Pumpkin Perfection' in having a 30% taller plant habit, 45% less flowers and flowers that are pastel pink in color. 'Pumpkin Perfection' can be most closely compared to the cultivars 'Jewel of Desert Topaz' (U.S. Plant Pat. No. 23,492) and 'WOWDOY3' (U.S. Plant Pat. No. 25,600). 'Jewel of Desert Topaz' is similar to 'Pumpkin Perfection' in having orange flowers and a flowering period of late spring through fall. 'Jewel of Desert Topaz' differs from 'Pumpkin Perfection' in having less flowers that are darker orange in color, 23 flowers per 10-week old plant, a taller plant height varying between 56 cm and 71 cm and less floriferous re-bloom in fall. 'WOWDOY3' differs from 'Pumpkin Perfection' in having flowers that are 25% larger in size, less flowers; an average of 31 flowers per 10-week old plant, a taller plant height of 10 cm and a plant width of 91 cm. 'Pumpkin Perfection' can also be compared to cultivars with co-pending patent applications from the same breeding program that have the same blooming periods. 'Coconut Crush' differs from 'Pumpkin Perfection' in having white flowers, 'Fig Fusion' differs from 'Pumpkin Perfection' in having hot pink flowers, 'Banana Blast' differs from 'Pumpkin Perfection' in having yellow flowers, 'Saucy Strawberry' differs from 'Pumpkin Perfection' in having red-pink flowers, and 'Tangerine Tango' differs from 'Pumpkin Perfection' in having red-orange flowers.

BRIEF DESCRIPTION OF THE DRAWINGS

The following is a detailed description of the new cultivar as observed on 3-month-old plants of 'Pumpkin Perfection' as grown outdoors in two-quart containers in Hudsonville, Mich.

The photograph in FIG. 1 provides a top view of 'Pumpkin Perfection' in bloom.

Figure 1:
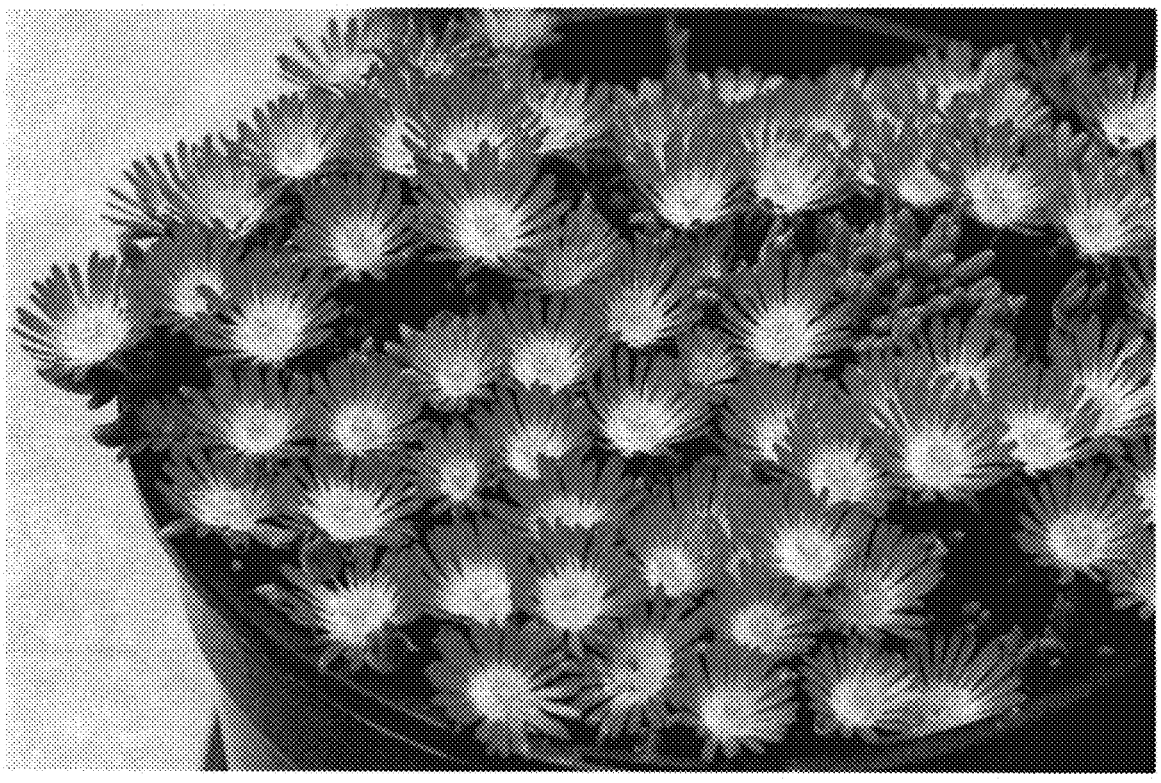
Figure 2:
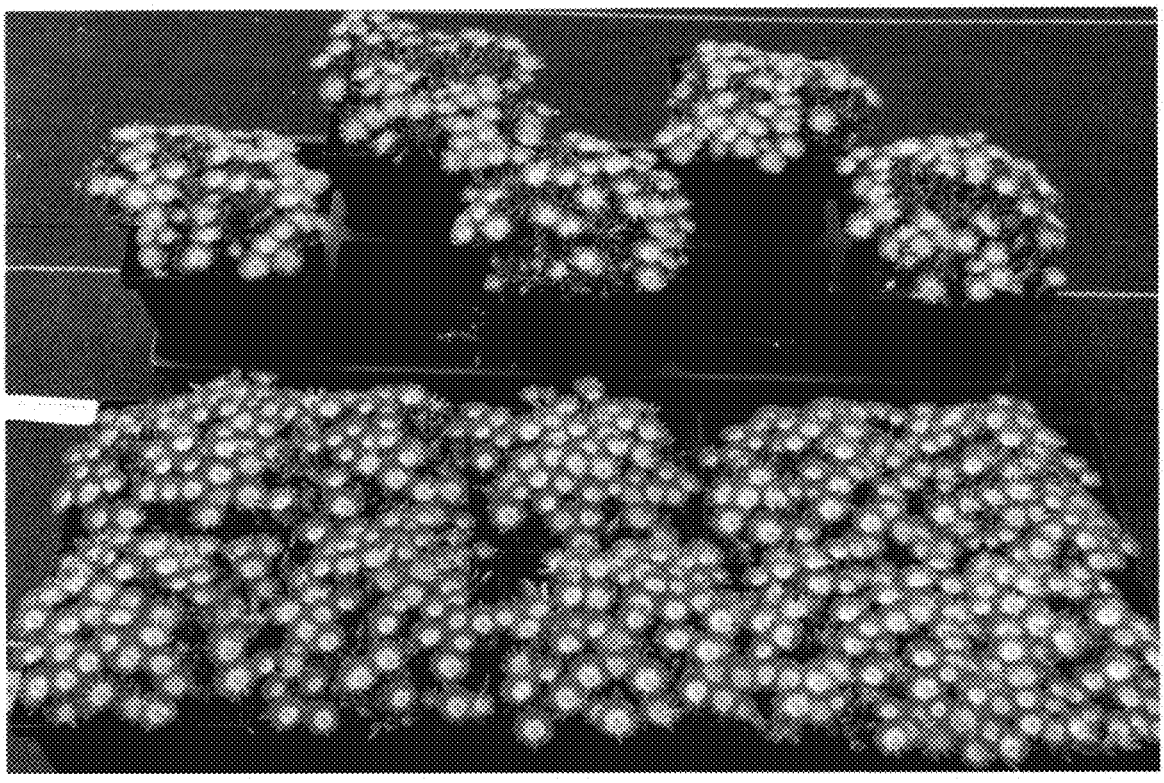

The photograph in FIG. 2 provides a comparison of 'Pumpkin Perfection' (bottom) and 'Jewel of Desert Topaz' (top). The colors in the photograph may differ slightly from the color values cited in the detailed botanical description, which accurately describe the colors of the new *Delosperma*.

DETAILED BOTANICAL DESCRIPTION

The following is a detailed description of 3-month-old plants of the new cultivar as grown in 9-cm containers outdoors in Hudsonville, Mich. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period.*—Blooms heavily from June 1 through late July, then re-blooms through late October in Michigan.

*Plant type.*—Herbaceous perennial.

*Plant habit.*—Clumping and mounded, compact ground cover.

*Plant type.*—Herbaceous perennial.

*Plant habit.*—Clumping, tightly mounded, compact ground cover.

*Height and spread.*—An average of 3.8 cm in height and about 38 cm in diameter in the landscape.

*Hardiness.*—At least in U.S.D.A. Zones 6 to 9.

*Diseases and pests.*—No susceptibility or resistance to diseases or pests has been observed.

*Root description.*—Fibrous roots, 199A in color.

*Root development.*—Cuttings root uniformly in 128-cell plugs in 6 weeks, 128-cell planted into a 9-cm pot or quart pot will finish and be in full bloom at 9 to 10 weeks after planting.

*Propagation.*—Stem tip cuttings.

*Growth habit.*—Moderate.

Stem description:

*Shape.*—Round.

*Stem color.*—Young stems; 192A, flushed with 176A, older stems 199A.

*Stem size.*—Lateral branches; an average of 3.5 cm in length and 1 mm in diameter.

*Internode length.*—An average of 2.3 mm.

*Stem substance.*—Succulent.

*Stem surface.*—Young; moderately glossy and glabrous, mature is woody.

*Stem strength.*—Young; moderately strong, mature; strong.

*Branching habit.*—Freely and very densely branching, both basal and lateral, an average of 10 lateral branches per basal stem (lateral branches grow from basal stems), 15 basal stems per plant (growing just above the soil).

Foliage description:

*Leaf shape.*—Ligulate, oblong and narrow.

*Leaf substance.*—Succulent, thick.

*Leaf division.*—Simple.

*Leaf base.*—Cuneate.

*Leaf apex.*—Acute.

*Leaf venation.*—None visible.

*Leaf margins.*—Entire.

*Leaf arrangement.*—Opposite to whorled.

*Leaf surface* (*upper and lower surface*).—Slightly glossy, sparsely to moderately pubescent with very short glandular hairs; too small to measure.

*Leaf color.*—Young; 146B, mature; 137C, base 145C.

*Leaf size.*—About 3 cm in length and 4 mm in width.

*Leaf quantity.*—Average of 26 per lateral branch.

*Leaf attachment.*—Sessile.

Inflorescence description:

*Inflorescence type.*—Flowers solitary, terminal.

*Flower number.*—Densely floriferous, quantity ranges, 9 per lateral stem

*Flower fragrance.*—Faint, sweet and pleasant.

*Flower aspect.*—Mostly held upright.

*Flower longevity.*—A few days, self-cleaning.

*Flower type.*—Single.

*Flower size.*—Average of 1 cm in diameter and depth.

*Flower buds.*—Broadly ovate to oblong in shape, an average of 1 in diameter and depth, color; N138A, flushed at sepal portion 148A.

*Calyx.*—Rotate in shape, average of 4 mm in depth and 1 cm in diameter.

*Sepals.*—5, rotate, narrowly ovate in shape, margin entire, an average of 5 mm in length and 1 mm in width, acute apex, cuneate base, both surfaces matte, inner and outer surface is 139B in color.

*Petals.*—An average of 30 per flower, rotate and slightly curved downward, narrowly oblanceolate in shape, surface is smooth and glossy on both surfaces, margin entire, apex acute, base cuneate, an average of 7 mm in length and 1 mm in width, color; opening flowers upper and lower surface; 187A, fully opened flower upper surface; 67A and suffused with 33A, tips 63A, fading to 28B with tips NN78A, fully opened flower lower surface; a blend of N74A, N78A and hints of 33A.

Petaloids.—An average of 30 per flower, rotate and near vertical surrounding stamens, lanceolate in shape, moderately to highly glossy on both surfaces, margin entire, apex acute, base cuneate, an average of 6 mm in length and 0.75 mm in width, color upper and lower surface; 16B, base NN155D.

*Peduncle.*—Average of 1 to 3.5 cm in length and 2 mm in diameter, held vertical to outwards, surface dull and glaucous, color; 151A, flushed with 182B.

*Pedicel.*—None.

Reproductive organs:

*Pistils.*—5, an average of 1 mm in length, pistil, style and stigma are not distinguishable, triangular shaped, 143B in color, ovary is 143B in color.

*Stamens.*—Average 60, anthers; dorsifixed and narrowly oblong in shape, an average of 0.5 mm in diameter, 8A in color, filaments are up to 5 mm in length NN155D in color, pollen is high in quantity and 8A in color.

*Fruit.*—Fruit and seed production was not observed under the conditions tested.

It is claimed:

1. A new and distinct variety of *Delosperma* plant named 'Pumpkin Perfection' as described and illustrated herein.

* * * * *